US006761691B2

(12) United States Patent
Tsuzuki

(10) Patent No.: US 6,761,691 B2
(45) Date of Patent: Jul. 13, 2004

(54) IMAGE FORMING METHOD USED IN ULTRASONIC DIAGNOSIS, ULTRASONIC DIAGNOSTIC APPARATUS, SIGNAL PROCESSING APPARATUS, AND RECORDING MEDIUM FOR RECORDING SIGNAL PROCESSING PROGRAM

(75) Inventor: Hirohiko Tsuzuki, Minami-Ashigara (JP)

(73) Assignee: Fuji Photo Film Co., Ltd., Kanagawa (JP)

( * ) Notice: Subject to any disclaimer, the term of this patent is extended or adjusted under 35 U.S.C. 154(b) by 120 days.

(21) Appl. No.: 09/907,577

(22) Filed: Jul. 19, 2001

(65) Prior Publication Data

US 2002/0045821 A1 Apr. 18, 2002

(30) Foreign Application Priority Data

Jul. 21, 2000 (JP) ...................................... 2000-220762
Jul. 21, 2000 (JP) ...................................... 2000-220763
Aug. 7, 2000 (JP) ...................................... 2000-238298

(51) Int. Cl.[7] ................................................ A61B 8/14
(52) U.S. Cl. ......................... 600/458; 600/443; 600/437
(58) Field of Search ................................. 600/437–472

(56) References Cited

U.S. PATENT DOCUMENTS

| 4,766,905 A | * | 8/1988 | Namekawa ................ 600/454 |
| 5,217,017 A | * | 6/1993 | Matsushima ............... 600/447 |
| 5,706,819 A | | 1/1998 | Hwang et al. |
| 5,833,614 A | * | 11/1998 | Dodd et al. ................ 600/447 |
| 5,891,038 A | * | 4/1999 | Seyed-Bolorforosh et al. .. 600/447 |
| 5,902,243 A | * | 5/1999 | Holley et al. ............... 600/443 |
| 5,913,823 A | * | 6/1999 | Hedberg et al. ............ 600/443 |
| 6,190,322 B1 | * | 2/2001 | Clark ......................... 600/443 |
| 6,193,659 B1 | * | 2/2001 | Ramamurthy et al. ...... 600/443 |
| 6,221,018 B1 | * | 4/2001 | Ramamurthy et al. ...... 600/443 |
| 6,302,845 B2 | * | 10/2001 | Shi et al. .................... 600/438 |
| 6,322,512 B1 | * | 11/2001 | De Jong et al. ............ 600/458 |

FOREIGN PATENT DOCUMENTS

| JP | A9164138 | 6/1997 |
| JP | A11178824 | 7/1999 |
| JP | A20005167 | 1/2000 |

OTHER PUBLICATIONS

ICIN–The Interuniveristy Cardiology Institute of the Netherlands, Ultrasound contrast imaging, Progress Report, N. de Jong, www.icin.knaw.nl/projects21progressmyocardial.html.*
Frinking, Peter J.A.; Cepedes, E. Ignacio; de Jong, Nico, Multi–Pulse Ultrasound Contrast Image Based On A Decorrelation Detection Strategy, IEEE Ultrasonics Symposium 1998, p. 1787–1790.*

* cited by examiner

Primary Examiner—Francis J. Jaworski
Assistant Examiner—William C Jung
(74) Attorney, Agent, or Firm—Birch, Stewart, Kolasch & Birch, LLP

(57) ABSTRACT

An ultrasonic diagnostic apparatus by which an image having superior space resolution is obtained. The apparatus includes: first means for transmitting an ultrasonic wave, which is continued for at least two cycles, to an object to be inspected, and for detecting an echo signal which is produced by reflection of the transmitted ultrasonic wave from tissue of the object to be inspected to thereby obtain a detection signal; second means for delaying the detection signal by such a time duration corresponding to one cycle of the transmitted ultrasonic wave to thereby obtain a delayed detection signal; and third means for obtaining image information related to the tissue of the object to be inspected based upon a difference between the detection signal and the delayed detection signal.

20 Claims, 15 Drawing Sheets

IMAGE FORMING METHOD USED IN ULTRASONIC DIAGNOSIS, ULTRASONIC DIAGNOSTIC APPARATUS, SIGNAL PROCESSING APPARATUS, AND RECORDING MEDIUM FOR RECORDING SIGNAL PROCESSING PROGRAM

BACKGROUND OF THE INVENTION

1. Field of the Invention

The present invention generally relates to an image forming method used in ultrasonic diagnoses, and also to an ultrasonic diagnostic apparatus with employment of this image forming method. More specifically, the present invention is directed to such an image forming method available in ultrasonic diagnoses, while using ultrasonic waves having a plurality of continuous cycles (wavelengths). Furthermore, the present invention is related to a signal processing apparatus capable of processing a detection signal which is acquired by detecting ultrasonic waves, while forming an ultrasonic diagnostic image used in such an ultrasonic diagnosis, and also related to a recording medium for recording thereon a signal processing program.

2. Description of a Related Art

Currently, since ultrasonic diagnoses are capable of acquiring blood flow information as featured functions, these ultrasonic diagnoses could be considerably advanced with respect to chest portions and abdomen portions of living bodies, or patients. In particular, since ultrasonic imaging techniques using contrast media have been recently developed, more precise blood flow information may be acquired. In such an ultrasonic contrast imaging operation, a micro bubble contrast medium is mainly injected into a vein. This micro bubble contrast medium is produced by mixing a large number of micro bubbles whose diameters are selected to be 1 micrometer to several micrometers into a fluid. This micro bubble is made in such a manner that a harmless gas for a living body (for example, air, carbon fluoride, etc.) is filled into a shell made of a harmless substance for a living body (for instance, lecithin).

Japanese Laid-open Patent Application JP-A-9-164138 describes the ultrasonic diagnostic image processing method. That is, while the ultrasonic contrast medium made of very fine bubbles is injected into the blood flows and also ultrasonic pulses capable of breaking the very fine bubbles contained in the tissue are transmitted, this ultrasonic diagnostic image processing method can check as to how degree, the very fine bubbles are re-circulated within the tissue during a time duration by measuring the ultrasonic waves. This time duration is defined after the very fine bubbles are broken and a certain time interval has elapsed.

Also, in ultrasonic diagnostic image forming techniques, Doppler signals or higher harmonic signals are advantageously utilized, and thus, blood flow information may be acquired from larger numbers of tissue of living bodies. In particular, since such an ultrasonic diagnostic image forming technique is combined with an ultrasonic contrast imaging technique, movement of blood flows can be more precisely estimated.

On the other hand, Japanese Laid-open Patent Application JP-A-11-178824 discloses the pulse inversion Doppler ultrasonic diagnostic image processing method. This pulse inversion Doppler ultrasonic diagnostic image processing method is realized by employing a transmission step of transmitting a sequence of modulated ultrasonic waves into the human body, and of producing the phase difference to the ultrasonic echoes acquired in response to this ultrasonic wave transmission; a reception step of receiving a set of the ultrasonic echo signals in response to the transmitted sequence; and a analysis step of analyzing this signal set in order to separate the phase shift information of the linear signal component from the phase shift information of the non-linear signal component.

However, while such a Doppler signal is detected, since the strong signals originated from the tissue having large movement (e.g., cardiac muscle) and also the higher harmonic signals generated from the tissue itself are mixed into this Doppler signal, it is impossible to detect the micro bubbles present in the blood vessels only, by this pulse inversion Doppler ultrasonic diagnostic image processing method.

Also, U.S. Pat. No. 5,706,819 describes such an ultrasonic diagnostic image processing method that since the influence caused by the higher harmonic contrast medium is received while alternately inverting the polarity (phase), the higher harmonic component of the transmission signal can be suppressed and also the scattering components can be removed so as to detect the influence of the higher harmonic contrast medium.

However, in order to execute such a higher harmonic image processing operation, a plurality of ultrasonic waves having the different polarities (different phases) are required to be transmitted. As a result, lengthy measuring time would be required. When the object under measurement is moved during such lengthy measuring time, there is such a problem that the space resolution of the image would be lowered.

On the other hand, a so-called "sub-harmonic imaging" technique may be gradually brought into consideration. In this sub-harmonic imaging technique, while such an ultrasonic wave containing a plurality of continuous waves is transmitted to an object to be inspected, an image may be formed based upon sub-harmonic echoes which are produced only from micro bubbles contained in a blood vessel. Since a sub-harmonic component is produced only by chaos-like vibrations as well as a branching phenomenon of micro bubbles, the following merit may be conceived in accordance with such a sub-harmonic imaging technique. That is to say, images having higher contrast than that of a harmonic imaging technique may be produced in this sub-harmonic imaging technique.

With respect to sub-harmonic echoes of micro bubbles, such sub-harmonic echoes can be produced by using continuous ultrasonic waves, which is known from the document "Subharmonic backscattering from ultrasound contrast agents" written by P. M. Shankar et. al., J. Acoust. Soc. Am. 106(4), 1999, p. 2104–2110. To execute such a sub-harmonic imaging technique, an ultrasonic wave containing a plurality of continuous waves called as a burst wave may be employed.

However, when such a plurality of waves which are continued for a long time duration such as a burst wave are employed, one set of waves becomes long. As a result, there is another problem that the resulting space resolution of the image is lowered.

Also, Japanese Laid-open Patent Application JP-A-2000-5167 discloses the ultrasonic wave transmitting method. That is, while the ultrasonic wave having a plurality of continuous waves is transmitted, such an ultrasonic wave is transmitted in order to firmly produce sub-harmonic echoes. In this ultrasonic wave, there are provided such ultrasonic waves having the instantaneous sound pressure capable of breaking the micro balloons (micro bubbles) before/after at least one ultrasonic wave having the instantaneous sound pressure incapable of breaking the micro balloons.

However, the transmission/reception of the ultrasonic wave with employment of the sub-harmonic echoes still requires further improvements including the process operation of the detection signals.

As a method of detecting a sub-harmonic strength, such a method of FFT (fast Fourier transform)-processing a received waveform has been employed. However, since this FFT method requires length calculation time, there is such a problem that this FFT method is not suitable for such a real-time image display operation. On the other hand, in accordance with the method of deriving a frequency component of a sub-harmonic wave by filtering a detection signal by a filtering circuit, frequency components of such a sub-harmonic wave are sandwiched among fundamental waves and higher harmonic waves, and thus, these frequency components are present over a plurality of frequencies. As a consequence, it is practically difficult to extract only such sub-harmonic wave components.

SUMMARY OF THE INVENTION

The present invention has been made to solve these problems, and therefore, has a first object to provide both an image forming method and an ultrasonic diagnostic apparatus, capable of acquiring an image having superior space resolution in ultrasonic diagnoses.

Also, a second object of the present invention is to provide both an image forming method and an ultrasonic diagnostic apparatus, capable of producing sub-harmonic echoes in high certainty, and also capable of displaying sub-harmonic information in such a higher speed nearly equal to real time in ultrasonic diagnoses. Furthermore, a third object of the present invention is to provide a signal processing apparatus and a recording medium for recording thereon a signal processing program, which may be utilized in such an image forming operation.

To achieve the above-explained objects, an image forming method to be used in an ultrasonic diagnosis according to the present invention includes the steps of: (a) transmitting an ultrasonic wave, which is continued for at least two cycles, to an object to be inspected; (b) detecting an echo signal which is produced by reflection of the transmitted ultrasonic wave from tissue of the object to be inspected to thereby obtain a detection signal; (c) delaying the detection signal by such a time duration corresponding to one cycle of the transmitted ultrasonic wave to thereby obtain a delayed detection signal; and (d) obtaining image information related to the tissue of the object to be inspected based upon a difference between the detection signal and the delayed detection signal.

Also, a ultrasonic diagnostic apparatus according to the present invention includes: first means for transmitting an ultrasonic wave, which is continued for at least two cycles, to an object to be inspected, and for detecting an echo signal which is produced by reflection of the transmitted ultrasonic wave from tissue of the object to be inspected to thereby obtain a detection signal; second means for delaying the detection signal by such a time duration corresponding to one cycle of the transmitted ultrasonic wave to thereby obtain a delayed detection signal; and third means for obtaining image information related to the tissue of the object to be inspected based upon a difference between the detection signal and the delayed detection signal.

Furthermore, a signal processing apparatus according to the present invention for processing a detection signal which is obtained by that an ultrasonic wave continued for at least two cycles is transmitted to an object to be inspected and an echo signal produced by reflection of the transmitted ultrasonic wave from tissue of the object to be inspected is detected, includes: first means for delaying the detection signal by such a time duration corresponding to one cycle of the transmitted ultrasonic wave to thereby obtain a delayed detection signal; and second means for obtaining image information related to the tissue of the object to be inspected based upon a difference between the detection signal and the delayed detection signal.

In addition, a recording medium according to the present invention for recording signal processing program is readable by a CPU (central processing unit) and is recording a signal processing program for processing a detection signal which is obtained by that an ultrasonic wave continued for at least N/2 cycles within a predetermined time duration is transmitted to an object to be inspected and an echo signal produced by reflection of the transmitted ultrasonic wave from tissue of the object to be inspected is detected where N is an integer not less than four, the signal processing program causing the CPU to execute: delaying the detection signal by such a time duration corresponding to one cycle of the transmitted ultrasonic wave to thereby obtain a delayed detection signal; obtaining a difference signal between the detection signal and the delayed detection signal; obtaining, when N is equal to an even number, image information related to the tissue of the object to be inspected based upon a difference between the difference signal within a first predetermined time duration and the difference signal within a second predetermined time duration; and obtaining, when N is equal to an odd number, image information related to the tissue of the object to be inspected based upon a summation of the difference signal within the first predetermined time duration and the difference signal within the second predetermined time duration.

DESCRIPTION OF THE PREFERRED EMBODIMENTS

Figure 1:
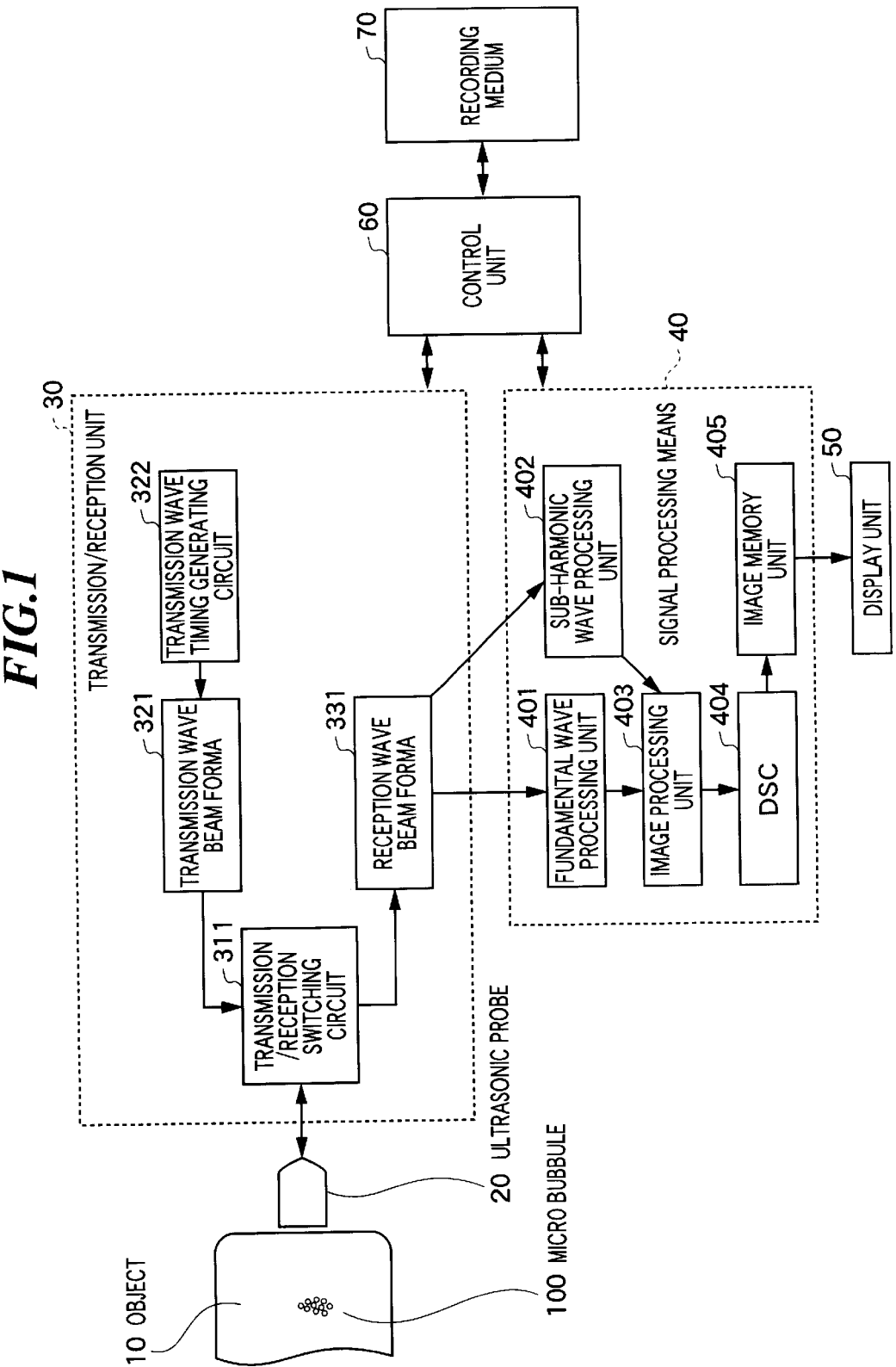
FIG. 1 is a block diagram for schematically indicating an ultrasonic diagnostic apparatus according to first and second embodiments of the present invention.

Referring now to drawings, various preferred embodiments of the present invention will be described in detail. It should be understood that the same reference numerals will be employed as those for denoting the same, or similar structural elements, and therefore, descriptions thereof are omitted.

FIG. 1 is a schematic block diagram for showing an arrangement of an ultrasonic diagnostic apparatus according to a first embodiment of the present invention.

As represented in FIG. 1, the ultrasonic diagnostic apparatus contains an ultrasonic probe 20 having an ultrasonic transducer array. The ultrasonic transducer array is constituted by a plurality of ultrasonic transducers. The ultrasonic probe 20 is used in such a manner that this ultrasonic probe 20 abuts against an object 10 to be inspected by an operator. It should be noted that while a micro bubble contrast medium has been previously injected into the object 10 to be inspected, a micro bubble 100 is contained in this object 10 to be inspected.

The ultrasonic probe 20 is connected to a transmission/reception unit 30. In the transmission/reception unit 30, a transmission wave timing generating circuit 322 generates a transmission wave timing signal in a periodic manner, and then supplies the transmission wave timing signal to a transmission wave beam former 321. The transmission wave beam former 321 produces a plurality of driving signals (transmission wave beam forming signals), and then supplies these driving signals via a transmission/reception switching circuit 311 to the ultrasonic probe 20. These driving signals are used to drive a plurality of ultrasonic transducers employed in the ultrasonic probe 20, while maintaining a time difference. The waveforms of these driving signals are selected in such a manner that a sound-pressure waveform of a transmission ultrasonic wave may become a waveform which, will be explained later. A plurality of ultrasonic transducers which constitute a transmission wave aperture of the ultrasonic probe 20 transmit a plurality of ultrasonic waves toward the object 10 to be inspected. These plural ultrasonic waves own phase differences corresponding to the time differences of these driving signals. Since wave fronts of the plural ultrasonic waves are synthesized with each other, an ultrasonic beam is formed.

On the other hand, the ultrasonic probe 20 receives ultrasonic waves (echoes) which are reflected from the object 10 to be inspected, and converts the received ultrasonic waves into electric signals. Then, the ultrasonic probe 20 outputs these converted signals as echo signals (detection signals) via the transmission/reception switching circuit 311 to a reception wave beam former 331. As previously explained, a plurality of reception signals which are received by the plural ultrasonic transducers are converted into a plurality of detection signals which will then be entered into the reception wave beam former 331. These plural ultrasonic transducers constitute a reception wave aperture of the ultrasonic probe 20. The reception wave beam former 331 applies time differences to a plurality of detection signals so as to adjust phases thereof, and thereafter, adds the phase-adjusted detection signals to each other so as to form an echo signal along a sound ray, namely, to execute beam-forming of the reception wave. Also, the sound ray of the reception wave is scanned by the reception wave beam former 331 in conjunction with the transmission wave.

Figure 2:
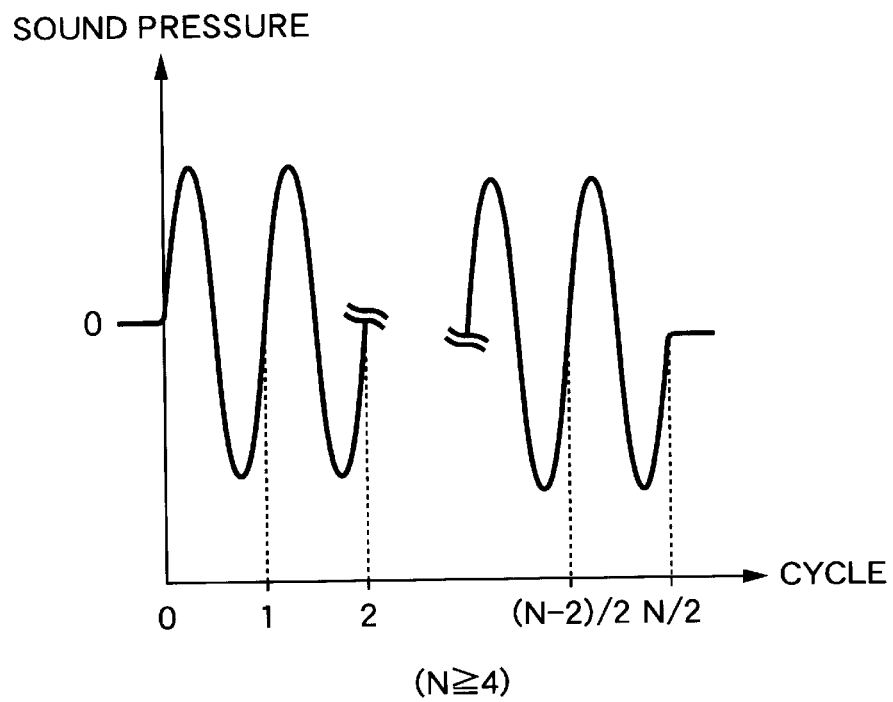
FIG. 2 is a graphic diagram for representing a sound pressure waveform of ultrasonic waves transmitted from the ultrasonic diagnostic apparatus according to the first embodiment of the present invention.

An ultrasonic (wave) beam transmitted by the ultrasonic probe 20 is set in such a manner that a continuous ultrasonic wave is produced by which, for example, a sound pressure waveform as shown in FIG. 2 may be produced at a focused region of this ultrasonic beam. As indicated in FIG. 2, this sound pressure waveform constitutes such a continuous wave which is continued during N/2 cycles (wavelengths). It should be noted that N is an integer larger than, or equal to four. Preferably, the condition is defined by $2<N/2<5\times10^4$. This continuous wave contains waves having such cycles larger than, or equal to 2 cycles, and less than, or equal to 50,000 cycles. The reason why the continuous wave is made longer than, or equal to 2 cycles is given as follows: since a difference between a detection signal and a delayed detection signal is calculated in a signal processing operation (will be explained later), a time duration which a transmission oscillator may become stable is required. Also, the reason why the continuous wave is made shorter than, or equal to 50,000 cycles is given as follows. That is, ultrasonic waves which are reflected from the object to be inspected do not constitute disturbance. It should also be noted that when an ultrasonic wave having a frequency of 1 MHz is employed, the above-explained 50,000 cycles corresponds to 1/20 seconds. Also, an upper limit of cycle numbers of the continuous wave may be preferably selected to be smaller than, or equal to 10,000 wavelengths, and more preferably selected to be smaller than, or equal to 1,000 wavelengths.

Figure 3:
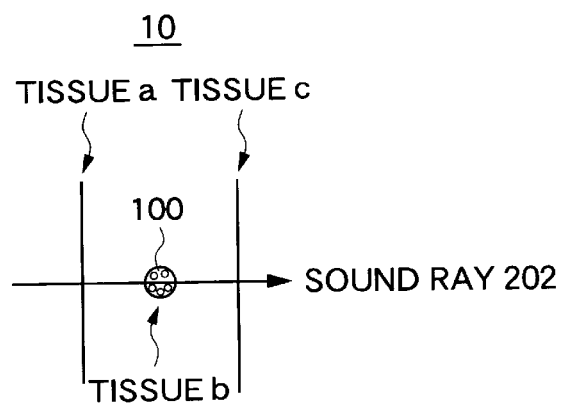
FIG. 3 illustratively shows a condition under which ultrasonic waves transmitted from the ultrasonic diagnostic apparatus are entered into an object to be inspected.

The ultrasonic waves having such a waveform is entered into tissue of the object 10 to be inspected as shown in FIG. 3, and then, ultrasonic waves (echo) reflected from the object 10 to be inspected are entered into the ultrasonic probe 20. As shown in FIG. 3, the object 10 to be inspected contains tissue "a", another tissue "b", and further tissue "c". For instance, both the tissue "a" and "c" are cells, whereas the tissue "b" is a blood vessel. The micro bubble 100 has been injected into an interior portion of the tissue "b". A sound ray 202 of a transmission ultrasonic wave passes through the tissues "a", "b", and "c", and a portion of the transmission ultrasonic wave is reflected from the tissue "a", two walls of the tissue "b", and the tissue "c". Also, another portion of the transmission ultrasonic wave is reflected from the micro bubble 100 which is located inside the tissue "b", so that a sub-harmonic component is produced. In this case, image information at different positions along a depth direction may be selectively acquired by specifying such time duration after the transmission ultrasonic wave is emitted and until the reflection wave is received.

Figure 4:
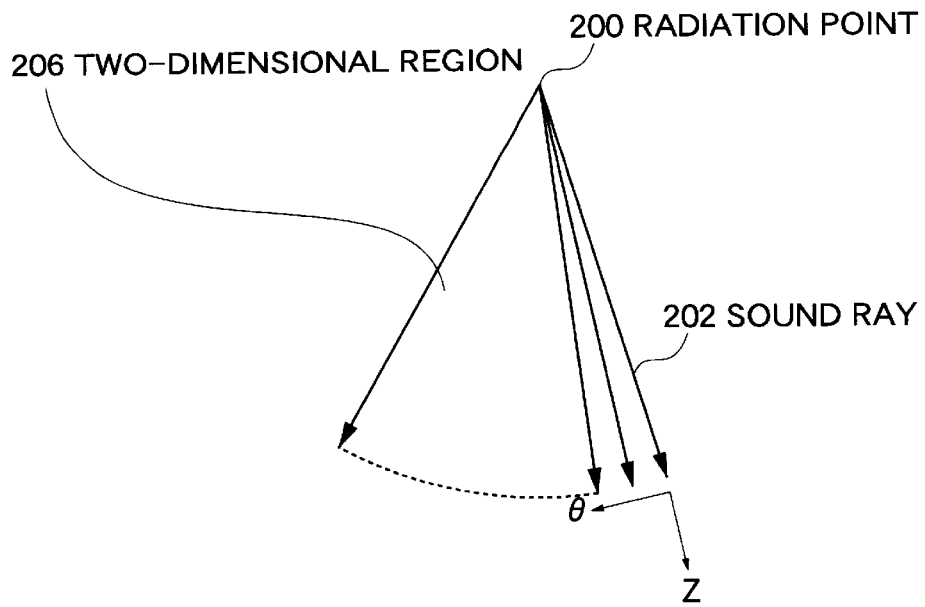
FIG. 4 is an explanatory diagram for explaining one example of a sound ray scanning operation executed in the ultrasonic diagnostic apparatus according to first to third embodiments of the present invention.

The transmission of the ultrasonic beam is repeatedly carried out in a predetermined time interval in response to the transmission wave timing signal which is generated from the transmission wave timing generating circuit 322 indicated in FIG. 1. The direction of the ultrasonic beam is sequentially changed by the transmission wave beam former 321. As a consequence, an interior portion of the object 10 to be inspected is scanned by the sound ray formed by the ultrasonic beam. In other words, in the interior portion of the object 10 to be inspected, the direction of the sound ray is sequentially changed. The transmission/reception unit 30 having such an arrangement may perform such a scanning operation, for example, as shown in FIG. 4. In FIG. 4, the ultrasonic beam (sound ray 202) which is extended from a radiation point 200 to the Z-direction scans a two-dimensional fan-shaped region 206 along the X-direction, namely, performs a so-called "sector scanning" operation.

Figure 5:
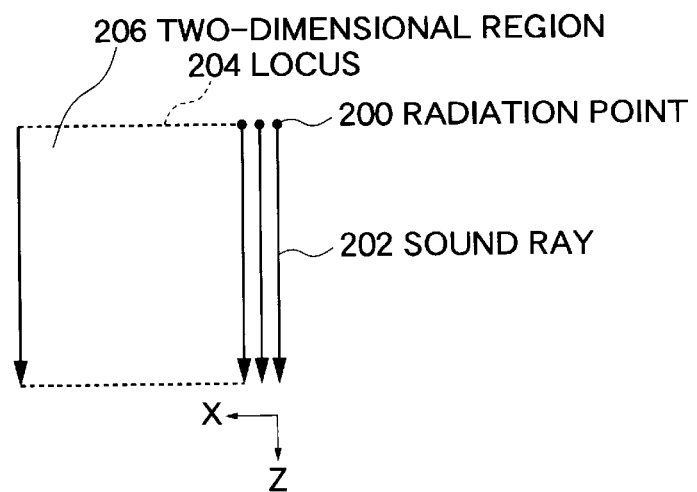
FIG. 5 is an explanatory diagram for explaining another example of a sound ray scanning operation executed in the ultrasonic diagnostic apparatus according to first to third embodiments of the present invention.

On the other hand, in such a case that both the transmission wave aperture and the reception wave aperture are formed by employing a portion of the ultrasonic transducer array are formed, since this aperture is sequentially moved along the ultrasonic transducer array, for instance, such a scanning operation as shown in FIG. 5 may be carried out. In FIG. 5, since the sound ray 202 which is extended from the projection point 200 along the Z-direction is moved in a parallel movement manner along an orbit 204 on a straight line, a two-dimensional rectangular region 206 is scanned along the X-direction, namely a so-called "linear scanning" operation is carried out.

Figure 6:
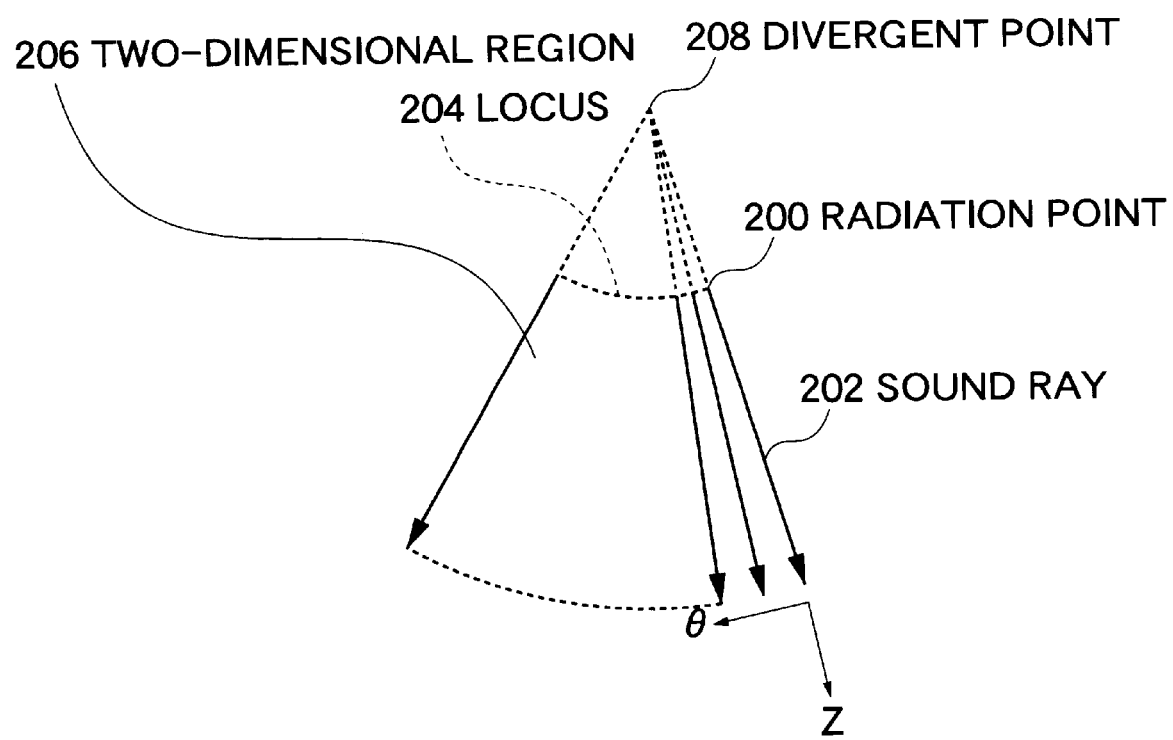
FIG. 6 is an explanatory diagram for explaining a further example of a sound ray scanning operation executed in the ultrasonic diagnostic apparatus according to first to third embodiments of the present invention.

Also, in such a case that the ultrasonic transducer array corresponds to a so-termed "convex array" which is formed along an arc shape projected along the transmission direction of the ultrasonic wave, for example, such a scanning operation as shown in FIG. 6 may be carried out by performing a similar sound-ray scanning operation to the above-explained linear scanning operation. In FIG. 6, a projection point 200 of a sound ray 202 is moved along an arc-shaped orbit 204 around a divergent point 208, and a two-dimensional region 206 having a fan shape is scanned along the θ-direction, namely, a so-called "convex scanning" operation is carried out.

Figure 7:
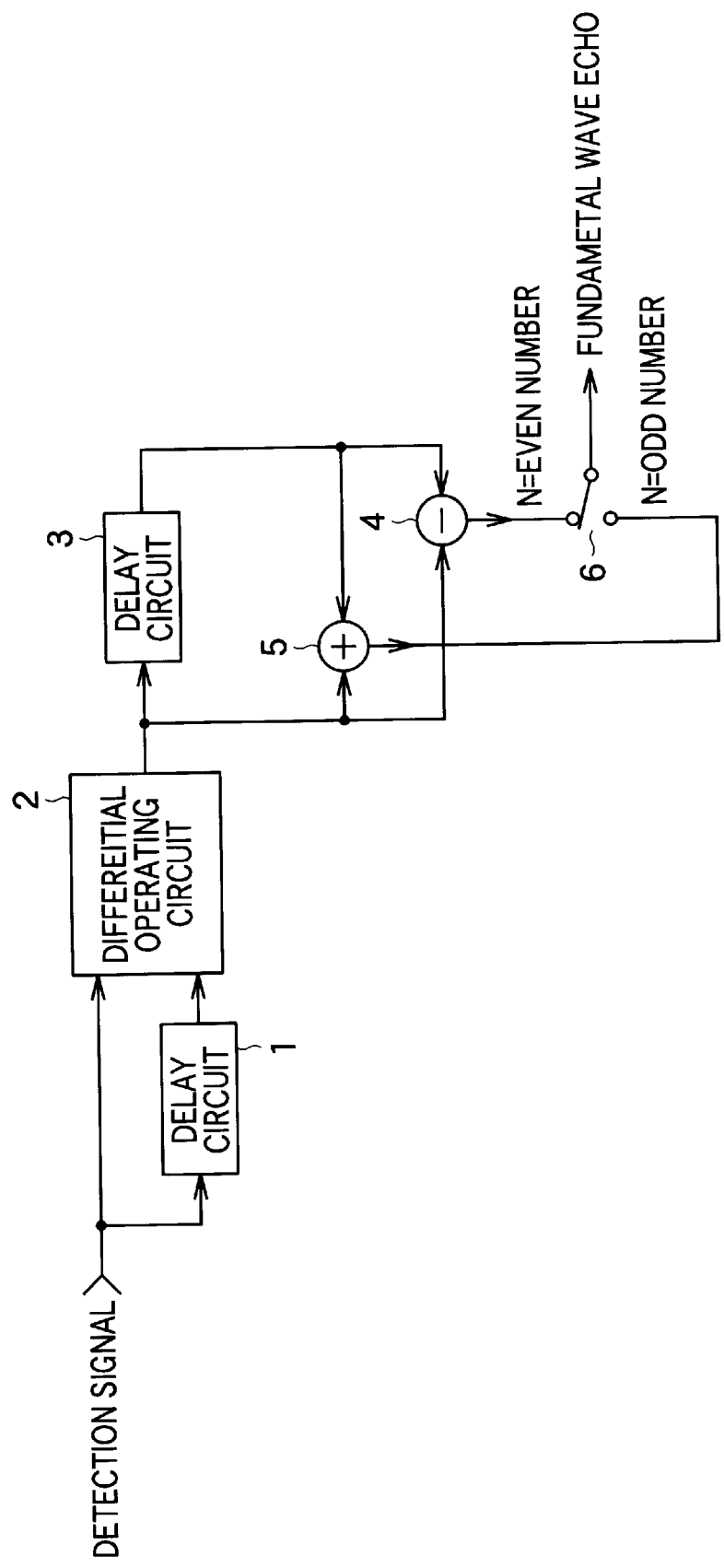
FIG. 7 is a block diagram for schematically indicating a portion of an arrangement of a fundamental wave processing unit shown in FIG. 1.

Returning back to FIG. 1, the reception wave beam former 331 is connected to both a fundamental wave processing unit 401 and a sub-harmonic wave processing unit 402, which are employed in the signal processing unit 40. Both the fundamental wave processing unit 401 and the sub-harmonic wave processing unit 402 process the input detection signals every sound ray, and then, supply the processed detection signals to an image processing unit 403. The image processing unit 403 produces a B-mode image by intensity modulating a strength of a reception wave based upon the processed detection signal. In this case, the basic wave processing unit 401 converts such a detection signal entered from the reception wave beam former 331 by using a method (will be discussed later), and thus, produces such a signal which is used to produce the B-mode image in the image processing unit 403. In this case, a fundamental wave is equal to a component having the same frequency as the fundamental frequency of the transmission ultrasonic wave. FIG. 7 schematically shows a portion of an internal arrangement of the above-described fundamental wave processing unit 401. In FIG. 7, a delay circuit 1 delays a detection signal by a fundamental cycle τ of a transmission wave. A differential operating circuit 2 outputs a difference signal between the detection signal and the delayed detection signal. Another delay circuit 3 delays this difference signal by one transmission time duration $T_0$ (namely, transmission time duration required to transmit an ultrasonic wave one time). A subtraction circuit 4 subtracts the delayed difference signal from the difference signal to obtain a difference, and an addition circuit 5 adds the difference signal to the delayed difference signal to obtain a summation. A selecting circuit 6 selects the output of the subtracting circuit 4 in the case that N is an even number, whereas the selecting circuit 6 selects the output of the adding circuit 5 in the case that N is an odd number, so that these selected output signals are derived as a fundamental wave echo signal. It should also be noted that the respective circuit arrangements of the fundamental wave processing unit 401 to the image processing unit 403 may be constituted by an analog circuit form, or a digital circuit form. Alternatively, these circuit arrangements may be constituted by employing software and a CPU (central processing unit). In this software case, a control unit 60 including the CPU may process a detection signal in accordance with a signal processing program recorded on a recording medium 70. As this recording medium 70, a floppy disk, a hard disk, an MO, an MT, a RAM, a CD-ROM, a DVD-ROM, and the like may be employed.

Figure 8:
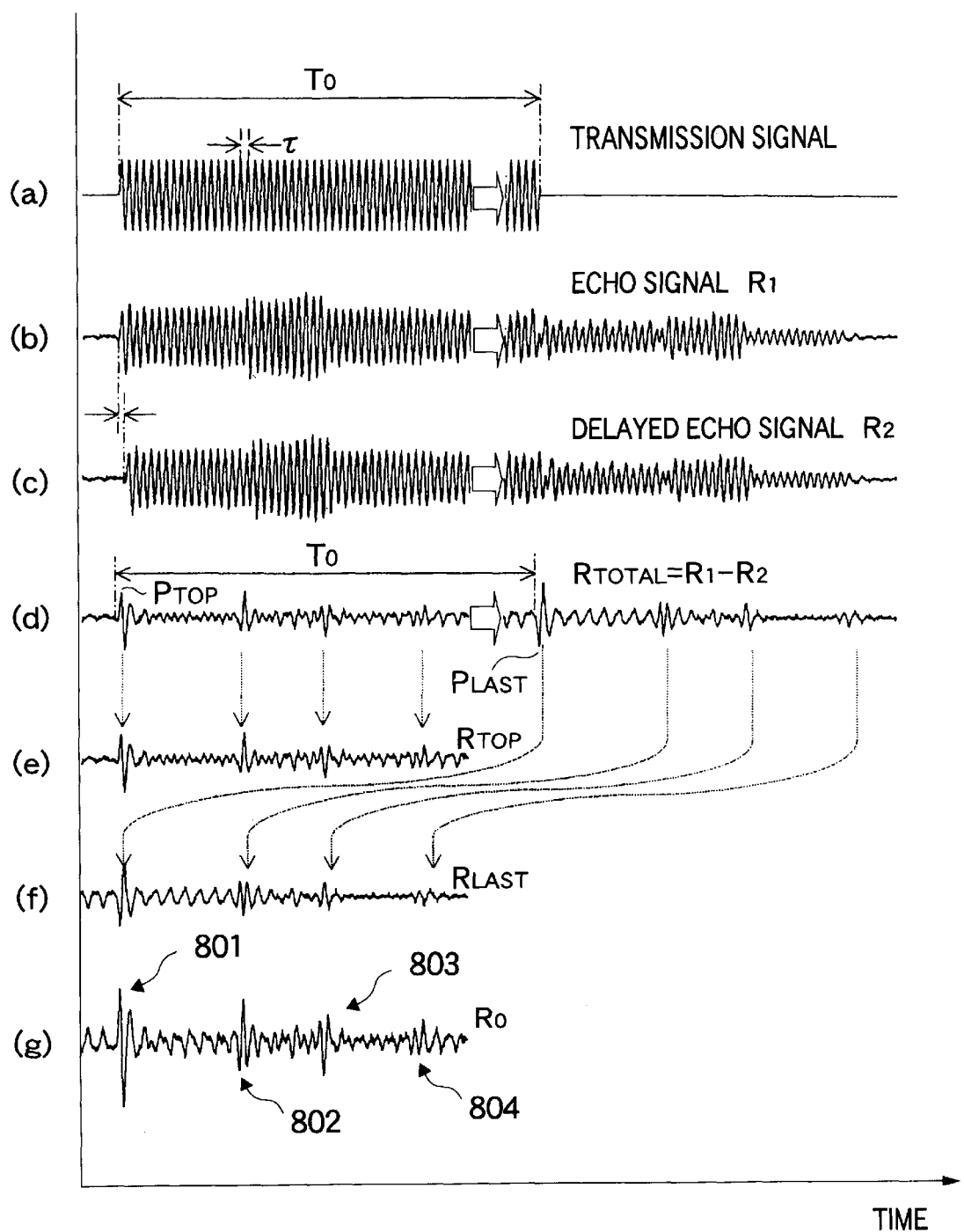
FIG. 8 is a waveform diagram for explaining a process operation of a detection signal by the fundamental wave processing unit shown in FIG. 1.

Next, operations of the fundamental wave processing unit 401 will now be explained with reference to FIG. 8. FIG. 8 is a waveform diagram for explaining process operations of the detection signal executed in the fundamental wave processing unit 401.

An item (a) of FIG. 8 represents a waveform of a transmission signal of an ultrasonic wave. The transmission ultrasonic wave owns such a structure that an ultrasonic wave having a fundamental cycle τ is continued by an N/2 wavelength during one transmission time duration $T_0$. It should be understood that N is an integer larger than, or equal to four. Such a transmission ultrasonic wave is entered into the object 10 to be inspected shown in FIG. 3.

An item (b) of FIG. 8 shows a waveform of an echo signal $R_1$. The echo signal $R_1$ is reflected from the tissue "a", "b", "c" of the object 10 to be inspected indicated in FIG. 3, and therefore, becomes complex. In the fundamental wave processing unit, the echo signal $R_1$ is delayed by the transmission wave fundamental cycle τ so as to produce a delayed echo signal $R_2$ indicated in an item (c) of FIG. 8.

Next, a difference between the echo signal $R_1$ and the delayed echo signal $R_2$ is calculated so as to produce a signal $R_{TOTAL}$ indicated in an item (d) of FIG. 8. In the case that N is equal to an even number, the signal $R_{TOTAL}$ produced in such a manner contains a pulse $P_{TOP}$ and another pulse $P_{LAST}$. The pulse $P_{TOP}$ is positioned at a head of a waveform which is continued during a first transmission time duration $T_0$. The pulse $P_{LAST}$ is positioned immediately after the first transmission time duration $T_0$, and the code of this pulse $P_{LAST}$ is inverted with respect to the code of the pulse $P_{TOP}$. On the other hand, in the case that N is equal to an odd number, the signal $R_{TOTAL}$ produced in such a manner contains a pulse $P_{TOP}$ and another pulse $P_{LAST}$. The pulse $P_{TOP}$ is positioned at the head of the waveform which is continued during the first transmission time duration $T_0$. The pulse $P_{LAST}$ is positioned immediately after the first transmission time duration $T_0$, and the code of this pulse $P_{LAST}$ is made coincident with respect to the code of the pulse $P_{TOP}$. In this case, the pulse $P_{TOP}$ is shifted from the pulse $P_{LAST}$ by one transmission time duration $T_0$ on the time axis. Accordingly, it is so assumed that a signal $R_{TOTAL}$ during a first transmission time duration is equal to a signal $R_{TOP}$ indicated in an item (e) of FIG. 8, and a signal $R_{TOTAL}$ during a second transmission time duration is equal to a signal $R_{LAST}$ indicated in an item (f) of FIG. 8.

Furthermore, in such a case that N is the even number, a difference ($R_{TOP}-R_{LAST}$) is obtained as a signal $R_0$ shown in an item (g) of FIG. 8, whereas in such a case that N is the odd number, a summation ($R_{TOP}+R_{LAST}$) is obtained as the signal $R_0$ indicated in the item (g) of FIG. 8. In the signals $R_0$ obtained in such a manner, a magnitude of a first pulse is equal to a summation of each of absolute values of these pulses $P_{TOP}$ and pulse $P_{LAST}$. Also, a scattering component 801 of the tissue "a", scattering components 802 and 803 at the two walls of the tissue "b", and a scattering component 804 of the tissue "c", as shown in FIG. 3, are extracted to be contained in the signal $R_0$. The signal $R_0$ calculated in the above-explained manner is assumed as the fundamental wave echo signal.

The fundamental wave processing unit 401 shown in FIG. 1 executes both a logarithmic amplifying operation and an envelope-detecting operation with respect to the fundamental wave echo signal which is acquired based upon the detection signal, so that a signal indicative of strengths of echoes at the respective reflection points on the sound ray, namely an A-scope signal may be obtained. The fundamental wave processing unit 401 forms B-mode image data, while instantaneous amplitudes at the respective time instants of the A scope signal are used as luminance values thereof. As explained above, the fundamental wave processing unit 401 produces the B-mode image data based upon the fundamental wave echo.

The sub-harmonic wave processing unit 402 shown in FIG. 1 executes both a logarithmic amplifying operation and an envelope-detecting operation with respect to the sub-harmonic wave signal which is acquired based upon the detection signal, so that a signal indicative of strengths of echoes at the respective reflection points on the sound ray, namely an A-scope signal may be obtained. The sub-harmonic wave processing unit 401 forms B-mode image data, while instantaneous amplitudes at the respective time instants of this A-scope signal are used as luminance values thereof. As explained above, the sub-harmonic wave processing unit 402 produces the B-mode image data based upon the sub-harmonic wave echo.

Both the fundamental wave processing unit 401 and the sub-harmonic wave processing unit 402 are connected to the image processing unit 403. The image processing unit 403 produces a plurality of B-mode images based upon the B-mode image data which are input from the fundamental wave processing unit 401 and the sub-harmonic wave processing unit 402, respectively. This operation will be explained later in detail.

The B-mode image data which are produced based upon both the fundamental wave echo signal and the sub-harmonic signal, input from the fundamental wave processing unit 401 and the sub-harmonic wave processing unit 402 respectively, are stored into a memory employed in the image processing unit 403. In this memory, sound ray data space for the respective B-mode image data is formed. A digital scan converter (DSC) 404 converts data obtained by scanning in the sound ray space into data obtained by scanning in the physical space. These image data are stored into an image memory 405, and are processed by an image processing processor in accordance with a predetermined data processing operation.

A display unit 50 is connected to the image memory 405. The display unit 50 displays thereon an image based upon the image data of the physical space stored in the image memory 405. Preferably, the display unit 50 is capable of displaying a color image.

Both the transmission/reception unit 30 and the signal processing unit 40 as shown in FIG. 1 are connected to the control unit 60. The control unit 60 supplies a control signal to the respective units so as to control the operations of these units. Also, various sorts of information signals derived from these units are input into the control unit 60. Under control of the control unit 60, ultrasonic imaging operation is carried out. The control unit 60 further contains an operation unit. While the operation unit is operated by an operator, this operation unit may enter a desirable instruction and desirable information into the control unit. The operation unit is constituted by, for example, a keyboard, or an operation panel equipped with other operating members.

Next, a description will now be made of operations of the ultrasonic diagnostic apparatus according to the first embodiment.

The operator manipulates the ultrasonic probe 20 so as to abut against a desirable position of the object 10 to be inspected, and then, manipulates the operation unit so as to perform ultrasonic imaging operation. Under control of the control unit 60, while the sound ray is sequentially scanned, the transmission/reception of the ultrasonic wave are carried out, so that the ultrasonic imaging operation is carried out. For instance, while the sound ray is sequentially scanned by way of the sector scanning form as represented in FIG. 4 in this ultrasonic diagnostic apparatus, the ultrasonic beam is transmitted every sound ray, and then, echoes thereof are received, so that a B-mode image is produced based upon the received echoes. Apparently, such a linear scanning operation as indicated in FIG. 5, or such a convex scanning operation as shown in FIG. 6 may be carried out. At this time, the transmitted ultrasonic beam contains, for example, such a sound pressure waveform shown in FIG. 2, and this ultrasonic beam may continuously vibrate the micro bubble 100, so that sub-harmonic echoes may be firmly produced.

In this ultrasonic diagnostic apparatus, B-mode image data is produced based upon the detection signals detected in the respective sound rays. The B-mode image data is produced in response to the fundamental wave echo signal, and further, the B-mode image data is produced in response to the sub-harmonic signal. These B-mode image data are stored into the memory employed in the image processing unit 403. Then, the image data which are stored in the memory provided in the image processing unit 403 are converted into data obtained by scanning in the physical space by the DSC 404, and thereafter, the converted image data are written into the image memory 405. The operator manipulates the operation unit so as to display these B-mode images which are displayed on the display unit 50.

Referring now to FIG. 1 and FIGS. 9–11, an ultrasonic diagnostic apparatus according to a second embodiment of the present invention will be described.

An overall arrangement of the ultrasonic diagnostic apparatus according to the second embodiment is similar to that of the first ultrasonic diagnostic apparatus shown in FIG. 1.

The second ultrasonic diagnostic apparatus owns such a feature with respect to a waveform of an ultrasonic wave which will be transmitted, and also operations of a sub-harmonic wave processing unit 402 employed a signal processing unit 40.

Figure 9:
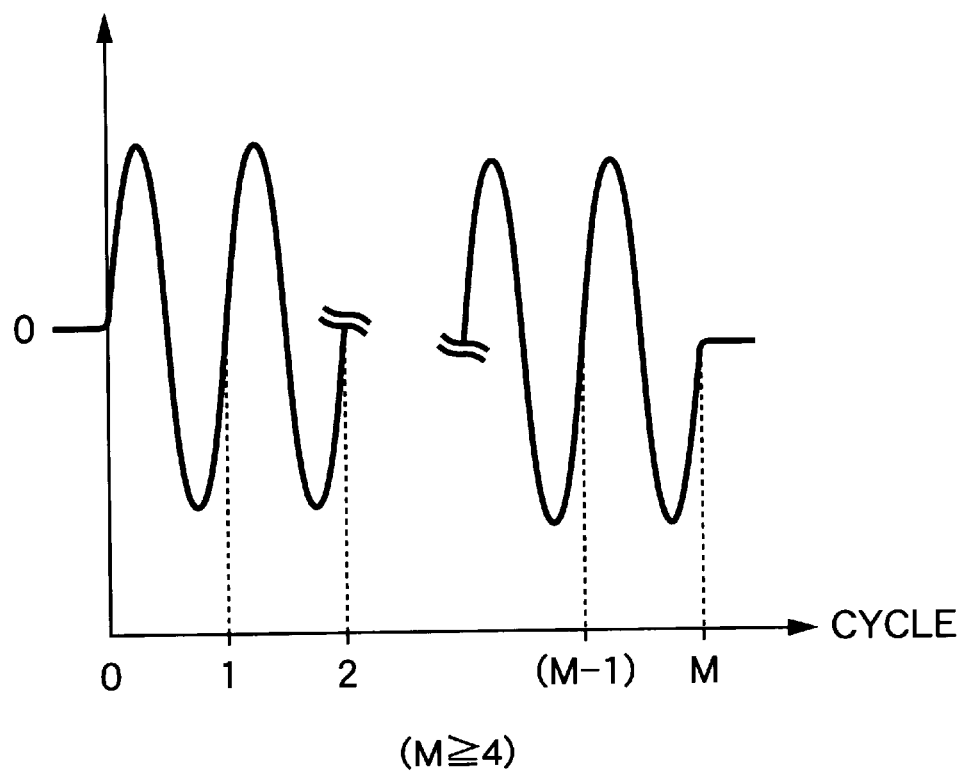
FIG. 9 is a graphic diagram for showing a sound pressure waveform of ultrasonic waves transmitted from the ultrasonic diagnostic apparatus according to the second and third embodiments of the present invention.

FIG. 9 represents a sound pressure waveform in a focusing region of an ultrasonic beam which is transmitted by an ultrasonic probe 20 according to the second embodiment. As indicated in FIG. 9, this sound pressure waveform constitutes such a continued during M cycles (wavelengths), and M is an integer larger than, or equal to 4. A sub-harmonic component corresponds to such a sound wave having a frequency K/L times as high as a transmission frequency. It should be noted that K and L are natural numbers which are provided independent from each other, and K/L is not equal to an integer. In particular, there is such a trend that a sound wave having a frequency of L=2 may strongly appear.

Figure 10A:
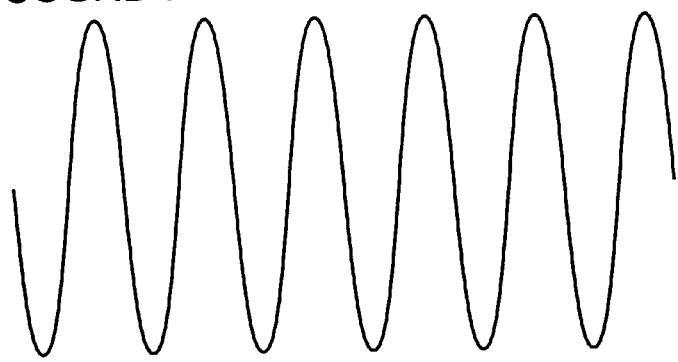
FIG. 10A and FIG. 10B are graphic diagrams for respectively representing a waveform of an ultrasonic wave transmitted from the ultrasonic diagnostic apparatus according to the second embodiment of the present invention, and an echo waveform of micro bubbles produced by this transmitted ultrasonic wave in a comparison manner.
Figure 10B:
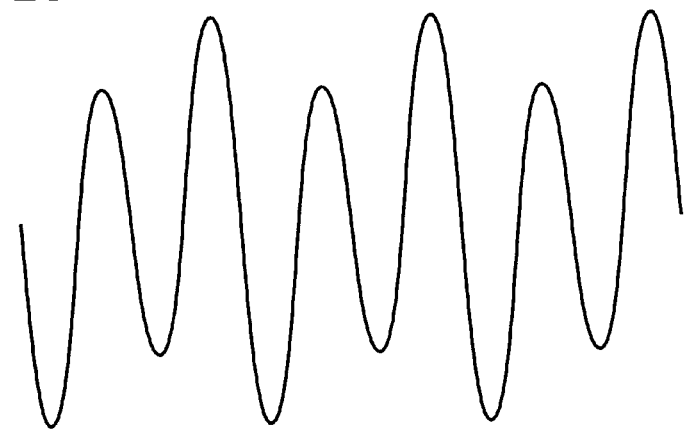

In the above-explained second embodiment, preferably, $4 \leq M \leq 5 \times 10^4$, and this continuous wave contains such waves having cycles larger than, or equal to 4 cycles, and less than, or equal to 50,000 cycles. In this case, the reason why this continuous wave is made longer than, or equal to 4 cycles is to realize such a condition that the sub-harmonic waves may be easily generated. Also, the reason why this continuous wave is made shorter than, or equal to 50,000 cycle is to avoid such a condition that waves reflected/returned from an object to be inspected never disturb this continuous wave. It should also be noted that when an ultrasonic wave having a frequency of 1 MHz is employed, 50,000 cycles correspond to 1/20 seconds. Also, an upper limit frequency of the continuous wave is preferably selected to be lower than, or equal to 10,000 wavelengths, and more preferably selected to be lower than, or equal to 1,000 wavelengths. FIG. 10A represents an example of a waveform of such a transmission ultrasonic wave. Also, FIG. 10B shows an example of an echo waveform of a micro bubble produced by this transmission ultrasonic wave.

Figure 11:
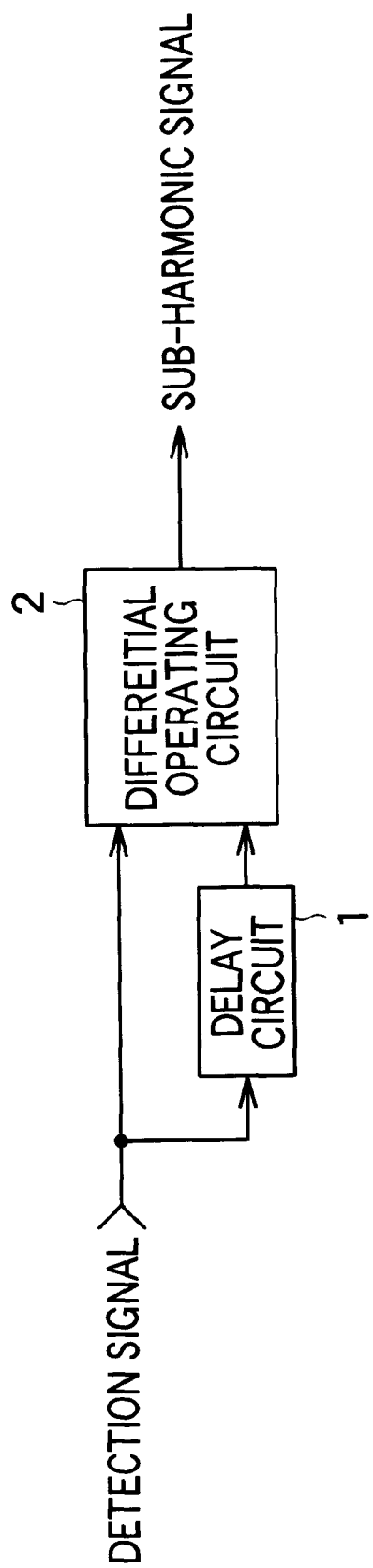
FIG. 11 is a block diagram for schematically showing a portion of an arrangement of a sub-harmonic wave processing unit indicated in FIG. 1.

FIG. 11 schematically shows a portion of an internal arrangement of the above-described sub-harmonic wave processing unit 402. In FIG. 11, a delay circuit 1 delays a detection signal by a fundamental cycle τ of a transmission signal. A differential operating circuit 2 calculate a difference between the detection signal and the delayed detection signal, so that a sub-harmonic signal is extracted to be outputted. It should be noted that similar to the first embodiment, the sub-harmonic wave processing unit 402 shown in FIG. 1 may be constituted by an analog circuit form or a digital circuit form. Alternatively, this circuit arrangement may be constituted by employing software and a CPU (central processing unit).

Figure 12:
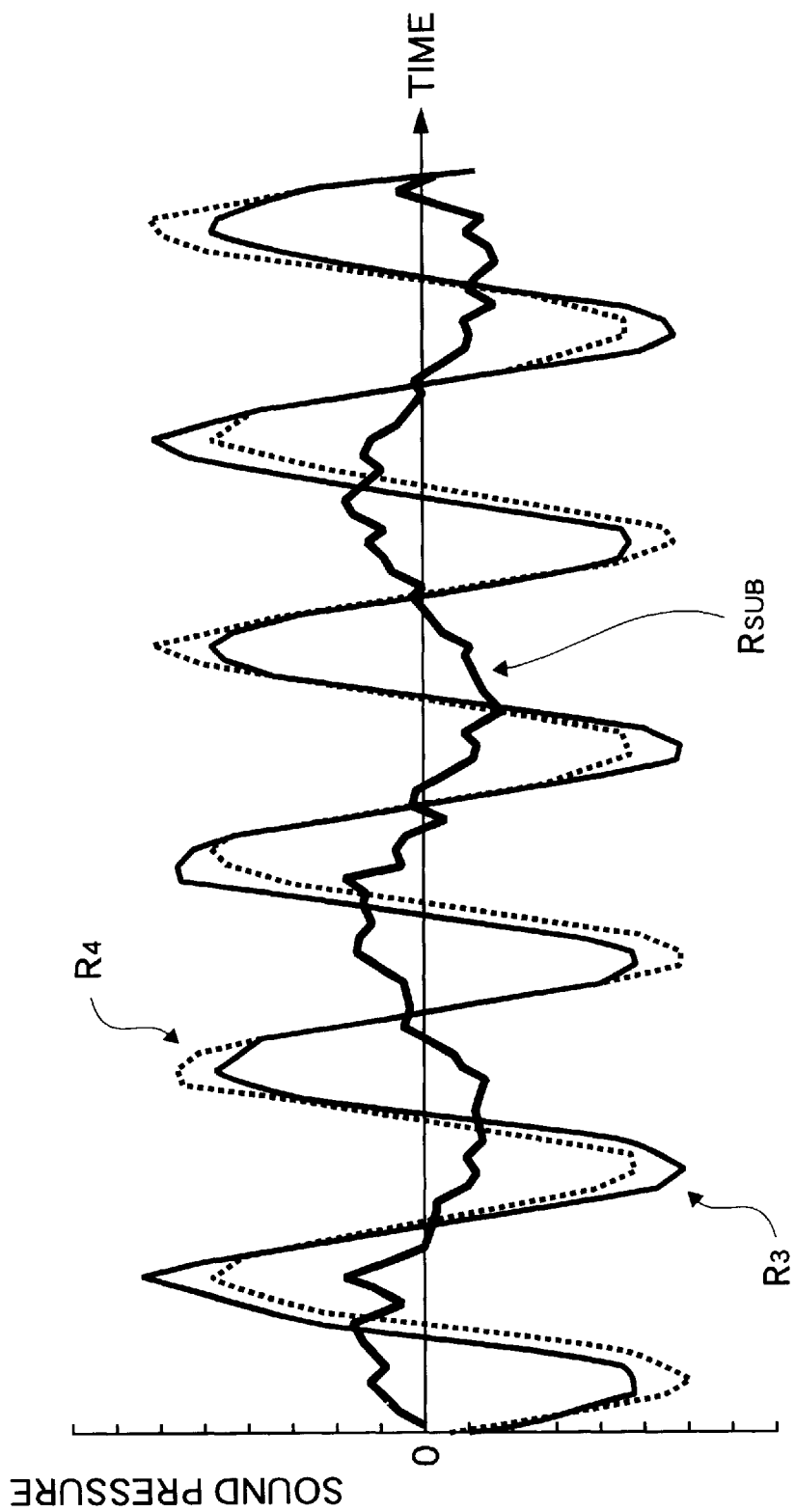
FIG. 12 is a waveform diagram for explaining a processing operation of a detection signal executed in the sub-harmonic wave processing unit shown in FIG. 1.

Next, operation of the sub-harmonic wave processing unit 402 will be explained with reference to FIG. 12. FIG. 12 is a waveform diagram for describing a process operation detection signal executed in the sub-harmonic wave processing unit 402.

In FIG. 12, there is shown such a detection signal $R_3$ of echoes produced by a micro bobble. This echo signal $R_3$ is delayed by a fundamental cycle τ of a transmission signal so as to produce a delayed echo signal $R_4$. Next, a difference between the echo signal $R_3$ and the delayed echo signal $R_4$ for a predetermined time duration is calculated so as to obtain a sub-harmonic signal $R_{SUB}$. An echo of a transmission ultrasonic wave is formed by summing a fundamental wave component, a higher harmonic component, and a sub-harmonic component. In this case, since both the fundamental wave component and the higher harmonic component correspond to such a waveform that the fundamental cycle τ of the transmission ultrasonic wave is used as a repetition unit, these fundamental wave component/higher harmonic component may be removed by performing the above-explained signal processing operations. As a result, only a sub-harmonic signal is left.

Referring back to FIG. 1, the reception wave beam former 331 outputs the detection signal to both the fundamental wave processing unit 401 and the sub-harmonic wave processing unit 402 employed in the signal processing unit 40.

The fundamental wave processing unit 401 indicated in FIG. 1 extracts a fundamental wave echo signal from the input detection signal, and executes both a logarithmic amplifying operation and an envelope-detecting operation with respect to this extracted fundamental wave echo signal, so that an A-scope signal is obtained. Then, the fundamental wave processing unit 401 produces B-mode image data based upon this acquired A-scope signal.

Also, the sub-harmonic wave processing unit 402 indicated in FIG. 1 extracts a sub-harmonic signal by employing the above-explained sub-harmonic echo extracting method, and further, executes both the logarithmic amplifying operation and the envelope-detecting operation with respect to this sub-harmonic signal in order to obtain an A-scope signal. In addition, the sub-harmonic wave processing unit 402 produces B-mode image data based upon this A-scope signal.

Thereafter, the signals which are processed by both the fundamental wave processing unit 401 and the sub-harmonic wave processing unit 402 are processed in a similar processing manner to that of the first embodiment of the present invention, so that a plurality of B-mode images are produced. Furthermore, these B-mode images are converted into data obtained by scanning in the physical space by the DSC 404, and then, the converted B-mode images are stored into the image memory 405 and also displayed on the display unit 50.

Figure 13:
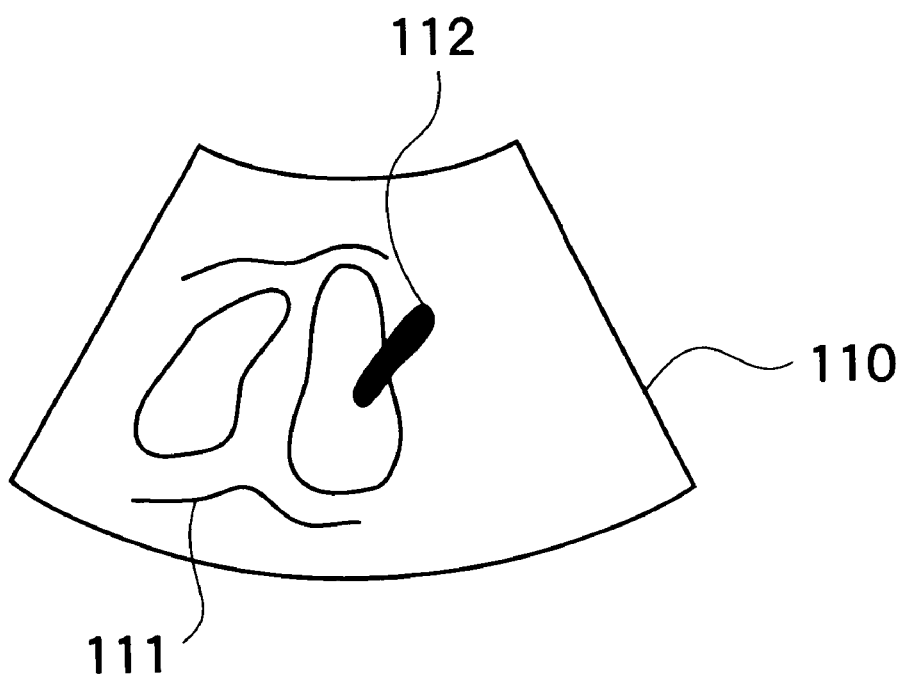
FIG. 13 is an illustration for indicating an example of an image displayed on the ultrasonic diagnostic apparatus according to the second embodiment.

FIG. 13 represents an example of an image displayed on the display unit 50. The display 110 of the display unit 50 displays thereon a synthesized image which is produced by synthesizing a tomographic image 111 of the tissue, which is acquired by the fundamental wave echo, with an image 112 which is acquired by the sub-harmonic echo of the micro bubble.

An ultrasonic diagnostic apparatus according to a third embodiment of the present invention will now be described with reference to FIGS. 14 and 15.

Figure 15:
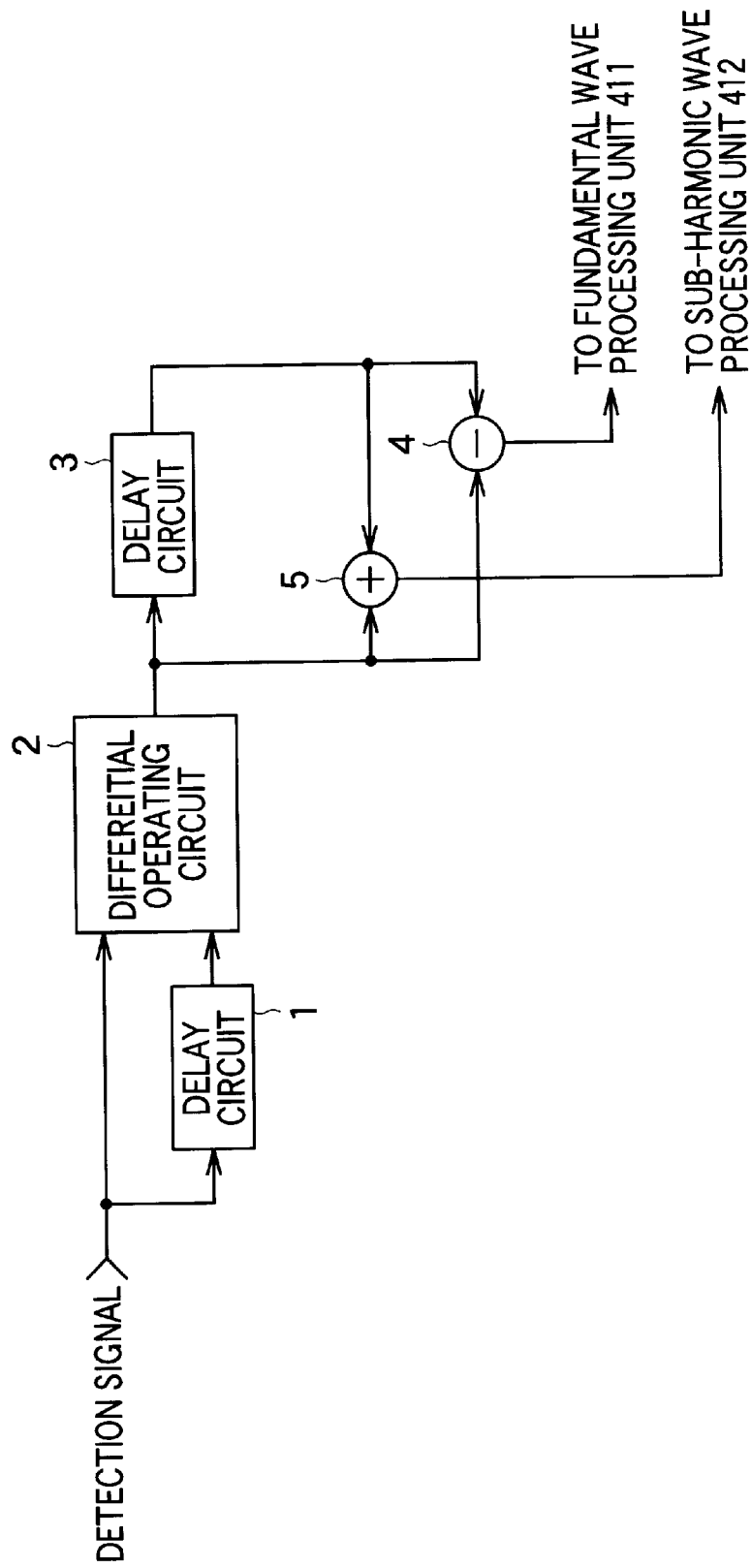
FIG. 15 is a block diagram for schematically indicating a portion of an arrangement of a waveform processing unit indicated in FIG. 14.

FIG. 15 is a schematic block diagram for representing an arrangement of an ultrasonic diagnostic apparatus according to the third embodiment. In this ultrasonic diagnostic apparatus, a signal processing unit 41 contains a waveform processing unit 400, a fundamental wave processing unit 411, and a sub-harmonic wave processing unit 412. Other structural units of the ultrasonic diagnostic apparatus are similar to those of the ultrasonic diagnostic apparatus according to the first embodiment of the present invention.

The waveform processing unit 400 separates both a fundamental wave component and a sub-harmonic component from an echo signal which is input from the reception wave beam former 331 every sound ray. Then, this waveform processing unit 400 supplies the fundamental wave component to the fundamental wave processing unit 411, and also supplies the sub-harmonic component to the sub-harmonic wave processing unit 412. Both the fundamental wave processing unit 411 and the sub-harmonic wave processing unit 412 process the entered fundamental wave component and the entered sub-harmonic wave component, and then, supply the processed fundamental wave/sub-harmonic wave components to the image processing unit 403.

In the ultrasonic diagnostic apparatus according to the third embodiment, an ultrasonic beam transmitted from the ultrasonic probe 20 is set so as to produce a continuous wave in a focusing region of this ultrasonic beam in such a manner that, for example, a sound pressure waveform similar to the sound pressure waveform shown in FIG. 9 may be formed. This sound pressure waveform constitutes such a continuous wave which is continued during M cycles (wavelengths), and M is an integer larger than, or equal to four. In this above-explained third embodiment, preferably, $4 \leq M < 5 \times 10^4$, and this continuous wave contains larger than, or equal to 4 cycles, and less than, or equal to 50,000 cycles. In this case, the reason why this continuous wave is made longer than, or equal to 4 cycles is to realize such a condition that the sub-harmonic waves may be easily generated. Also, the reason why this continuous wave is made shorter than, or equal to 50,000 cycles is to avoid such a condition that waves reflected/returned from an object to be inspected never disturb this continuous wave. It should also be noted that when an ultrasonic wave having a frequency of 1 MHz is employed, 50,000 cycles correspond to $\frac{1}{20}$ seconds. Also, an upper limit frequency of the continuous wave is preferably selected to be lower than, or equal to 10,000 wavelengths, and more preferably, selected to be lower than, or equal to 1,000 wavelengths.

FIG. 15 schematically shows a portion of an internal arrangement of the above-described waveform processing unit 400. In FIG. 15, a delay circuit 1 delays a detection signal by a transmission wave fundamental cycle τ. A differential operating circuit 2 outputs a difference signal between the detection signal and the delayed detection signal. Another delay circuit 3 delays this difference signal by one transmission time duration $T_0$. A subtracting circuit 4 subtracts the delayed difference signal from the difference signal to extract a fundamental wave component, and then, supplies this extracted fundamental wave component to the fundamental wave processing unit 411 shown in FIG. 14. Also, an adding circuit 5 calculates a summation between the difference signal and the delayed difference signal to extract a sub-harmonic component, and then, supplies this sub-harmonic component to the sub-harmonic wave processing unit 412 indicated in FIG. 14. It should also be understood that the respective constructive units of the waveform processing unit 400, the image processing unit 403, the fundamental wave processing unit 411, and the sub-harmonic wave processing unit 412 may be arranged by employing analog circuits or digital circuit in a similar manner to that of the ultrasonic diagnostic apparatus according to the first embodiment. Alternatively, these constructive units may be arranged by employing digital circuits, or by using both software and a CPU.

Figure 16:
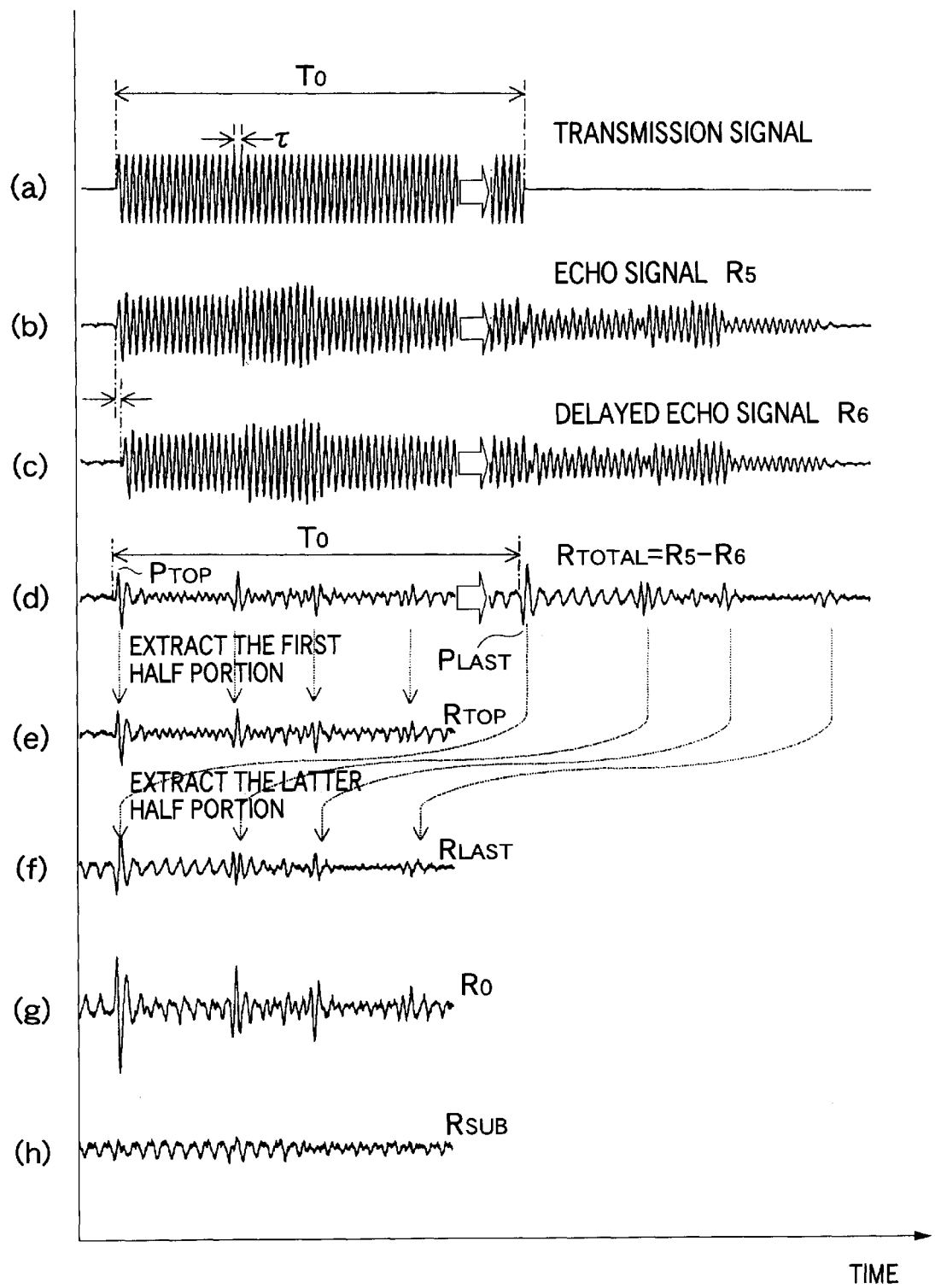
FIG. 16 is a waveform diagram for explaining a process operation of a detection signal in the waveform processing unit indicated in FIG. 14.

Subsequently, operations of the above-explained waveform processing unit 400 will now be explained with reference to FIG. 16 and FIG. 17. FIG. 16 is a waveform diagram for describing process operations of a detection signal executed in the waveform processing unit.

An item (a) of FIG. 16 represents a waveform of a transmission signal of an ultrasonic wave. The transmission ultrasonic wave owns such a structure that an ultrasonic wave having a fundamental cycle τ is continued by M wavelengths during one transmission time duration $T_0$ (namely, transmission time duration required to transmit ultrasonic wave one time). It should be understood that M is an integer larger than, or equal to four. Such a transmission ultrasonic wave is entered into the object 10 to be inspected shown in FIG. 3. An item (b) of FIG. 16 shows a waveform of an echo signal $R_5$. The reception wave, namely, the echo signal $R_5$ is reflected from the tissue "a", "b", "c" of the object 10 to be inspected indicated in FIG. 3 and from the micro bubble 100, and therefore, becomes complex. In the fundamental wave processing unit, the echo signal $R_5$ is delayed by the transmission wave fundamental cycle τ so as to produce a delayed echo signal $R_6$ indicated in an item (c) of FIG. 16.

Next, a difference between the echo signal $R_5$ and the delayed echo signal $R_6$ is calculated so as to produce a signal $R_{TOTAL}$ indicated in an item (d) of FIG. 16. The signal $R_{TOTAL}$ formed in such a manner contains a pulse $P_{TOP}$ another pulse $P_{LAST}$, and sub-harmonic components. The pulse $P_{TOP}$ is positioned at a head of a waveform which is continued during a first transmission time duration $T_0$. The pulse $P_{LAST}$ is positioned immediately after the first transmission time duration $T_0$, and the code of this pulse $P_{LAST}$ is inverted with respect to the code of the pulse $P_{TOP}$. A phase of the sub-harmonic component during the first transmission time duration $T_0$ is made coincident with a phase of the sub-harmonic component during the next transmission time duration. In this case, the pulse $T_{TOP}$ is shifted from the pulse $P_{LAST}$ by one transmission time duration $T_0$ on the time axis. Accordingly, it is so assumed that the signal $R_{TOTAL}$ which is removed by the transmission time duration $T_0$ from the last signal on the time axis is equal to such a signal $R_{TOP}$ as shown in an item (e) of FIG. 16. Also, the signal $R_{TOTAL}$ which is removed by the time duration $T_0$ from the first signal on the time axis is equal to such a signal $R_{LAST}$ as indicated in an item (f) of FIG. 16.

Furthermore, a difference ($R_{TOP} - R_{LAST}$) is calculated as a signal $R_O$ as shown in an item (g) of FIG. 16. In this signal $R_O$, the sub-harmonic component disappears, and this signal $R_O$ contains only a summation made between an absolute value of the signal $R_{TOP}$ and an absolute value of the signal $R_{LAST}$. The signal $R_O$ which is calculated in the above-explained manner is supplied to the fundamental wave processing unit 411 as a calculation result of the waveform processing unit 400 shown in FIG. 14.

Also, a summation ($R_{TOP} + R_{LAST}$) is calculated as a signal $R_{SUB}$ as indicated in an item (h) of FIG. 16. In this signal $R_{SUB}$, both the pulse $P_{TOP}$ and the pulse $P_{LAST}$ disappear, and this signal $R_{SUB}$ contains only the sub-harmonic component. The signal $R_{SUB}$ which is calculated in the above-explained manner is supplied to the sub-harmonic wave processing unit 412 as a calculation result of the waveform processing unit 400 indicated in FIG. 14.

Figure 14:
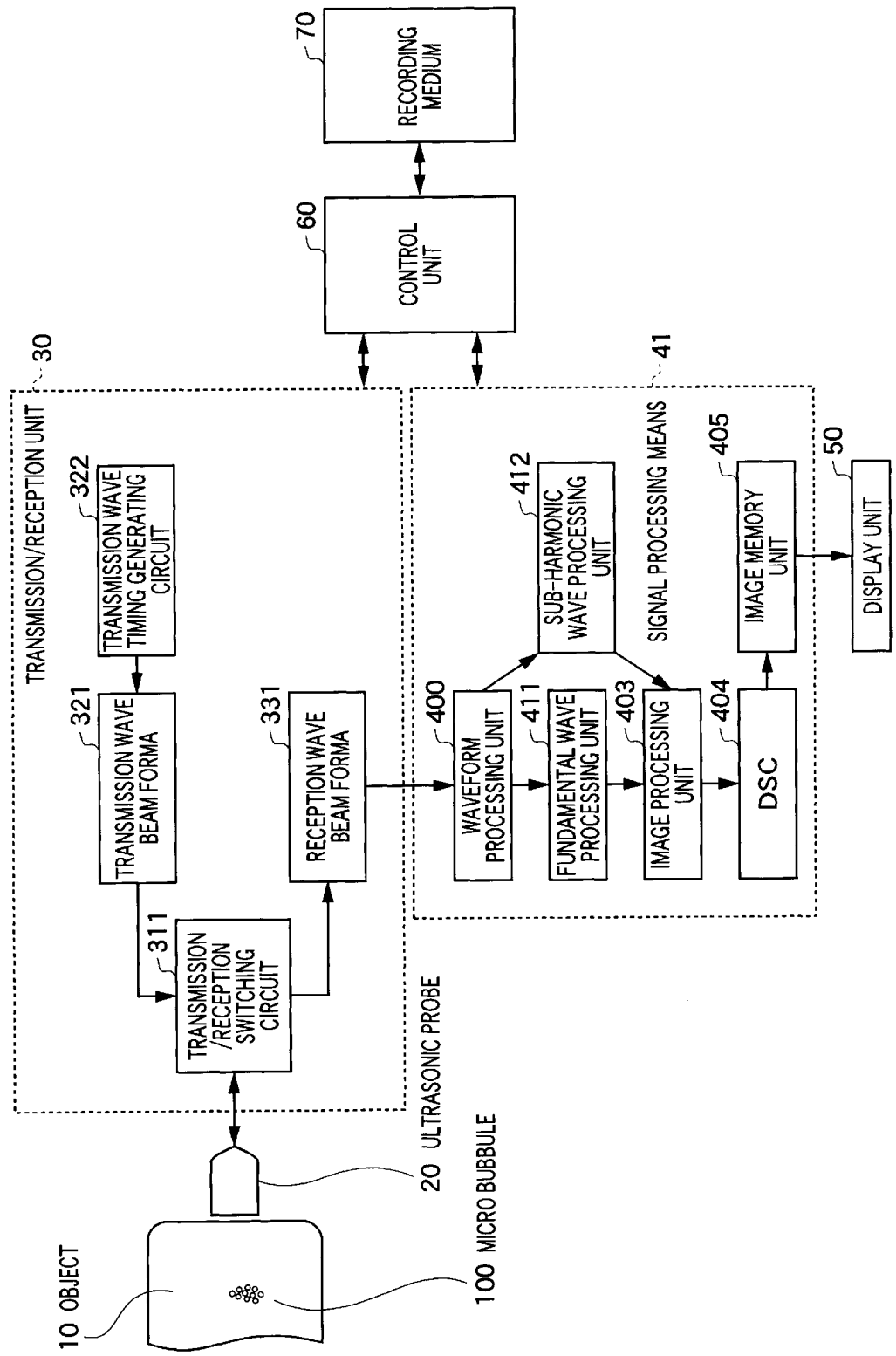
FIG. 14 is a block diagram for schematically representing an arrangement of an ultrasonic diagnostic apparatus according to a third embodiment of the present invention.

The fundamental wave processing unit 411 indicated in FIG. 14 contains a filter capable of filtering a fundamental wave echo. In other words, the filter is capable of causing such an echo signal to pass through this filter. The echo signal has the same frequency as the fundamental frequency of the transmission ultrasonic wave. The fundamental wave processing unit 411 executes both a logarithmic amplifying operation and an envelope-detecting operation with respect to a fundamental wave echo signal which is obtained from the detection signal so as to obtain an A-scope signal. Then, the fundamental wave processing unit 411 produces B-mode image data based upon this A-scope signal.

Figure 17:
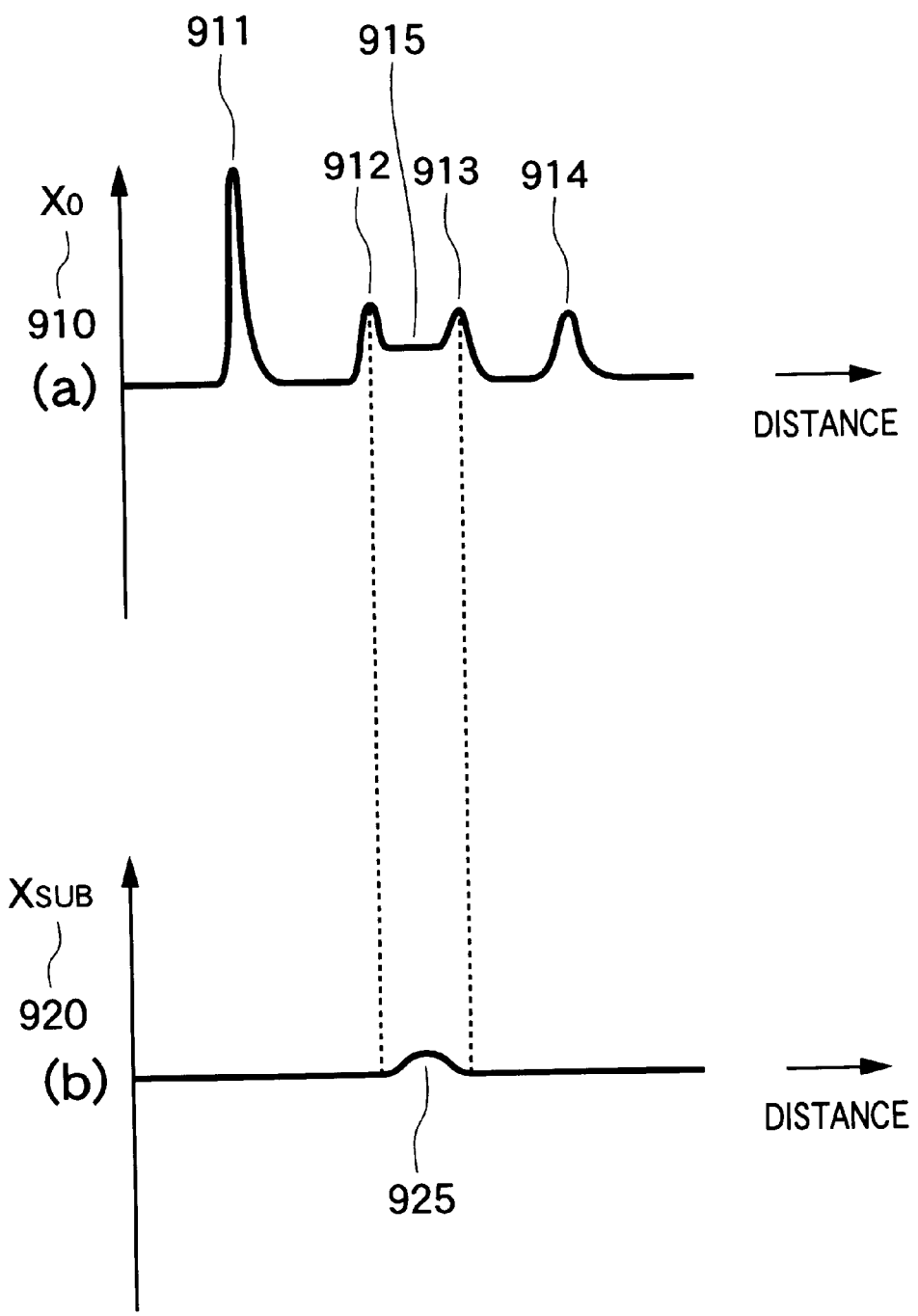
FIG. 17 is a graphic diagram for representing one-dimensional image data as a luminance signal, which is produced by the ultrasonic diagnostic apparatus according to the third embodiment of the present invention.

In this case, one-dimensional image data which is produced based on such a signal $R_O$ shown in an item (g) of FIG. 16 is represented as a luminance signal $X_O 910$ in an item (a) of FIG. 17. In this luminance signal $X_O 910$, a scattering component 911 of the tissue "a" indicated in FIG. 3, both scattering components 912 and 913 of two walls of the tissue "b" indicated in FIG. 3, a scattering component 914 of the tissue "c" indicated in FIG. 3, and a scattering component 915 of the micro bubble which is injected into the tissue "b" are extracted.

The sub-harmonic wave processing unit 412 shown in FIG. 14 executes both a logarithmic amplifying operation and an envelope-detecting operation with respect to the sub-harmonic signal which is acquired based upon the detection signal, so that an A-scope signal may be obtained, and also such a signal is produced in which instantaneous amplitudes at the respective time instants of this A-scope signal are used as luminance values of the respective time instants. Furthermore, this signal is converted into a change signal per unit distance on a distance axis so as to calculate an absolute value of a differentiation. As a result, B-mode image data is produced. As explained above, the sub-harmonic wave processing unit 412 produces the B-mode image data based upon the sub-harmonic echo.

In this case, one-dimensional image data which is produced based upon such a signal $R_{SUB}$ as shown in an item (h) of FIG. 16 is indicated as a luminance signal $X_{SUB}$920 in an item (b) of FIG. 17. In the luminance signal $X_{SUB}$920, a sub-harmonic signal 925 of a micro bubble which is injected into the tissue "b" shown in FIG. 3 is extracted.

Both the fundamental wave processing unit 411 and the sub-harmonic wave processing unit 412 are connected to the image processing unit 403. The image processing unit 403 produces a plurality of B-mode images based upon the B-mode image data which are entered from the fundamental wave processing unit 411 and the sub-harmonic wave processing unit 412, respectively. This operation is similar to the above-explained operation of the first embodiment of the present invention. Also, operations of the ultrasonic diagnostic apparatus used to execute the image forming method for the ultrasonic diagnosis according to the third embodiment are similar to those executed in the first embodiment of the present invention.

As previously described in detail, in accordance with the ultrasonic diagnostic apparatus, such an image having superior space resolution can be obtained, and also, the sub-harmonic information can be displayed at speeds approximated to real time.

While the above description has been made of such an example that the B-mode ultrasonic imaging operations are carried out by utilizing the continuous ultrasonic waves in the first to third embodiments, the ultrasonic imaging operation is not limited only to the B-mode imaging operation, but may be applied to such an imaging operation capable of acquiring an movement image by utilizing a Doppler shift of sub-harmonic echoes.

What is claimed is:

1. An image forming method to be used in an ultrasonic diagnosis, comprising the steps of:
   (a) transmitting an ultrasonic wave, which is continued for at least two cycles, to an object to be inspected;
   (b) detecting an echo signal which is produced by reflection of the transmitted ultrasonic wave from tissue of said object to be inspected to thereby obtain a detection signal;
   (c) delaying said detection signal by such a time duration corresponding to one cycle of the transmitted ultrasonic wave to thereby obtain a delayed detection signal; and
   (d) obtaining image information related to the tissue of said object to be inspected based upon a difference between said detection signal and said delayed detection signal.

2. An image forming method according to claim 1, wherein:
   step (a) includes transmitting to said object to be inspected, an ultrasonic wave which is continued for at least N/2 cycles within a predetermined time duration where N is an integer not less than four; and
   step (d) includes obtaining a difference signal between said detection signal and said delayed detection signal and obtaining, when N is equal to an even number, image information related to the tissue of said object to be inspected based upon a difference between said difference signal within a first predetermined time duration and said difference signal within a second predetermined time duration, whereas obtaining, when N is equal to an odd number, image information related to the tissue of said object to be inspected based upon a summation of said difference signal within the first predetermined time duration and said difference signal within the second predetermined time duration.

3. An image forming method according to claim 2, wherein:
   step (d) includes obtaining image information by using amplitudes of a signal at respective time instants as luminance values, said signal being acquired by logarithmic amplifying and also envelope-detecting one of said difference and said summation.

4. An image forming method according to claim 1, wherein:
   step (a) includes transmitting to said object to be inspected, an ultrasonic wave which is continued for at least four cycles; and
   step (d) includes extracting a sub-harmonic component of said echo signal based upon the difference between said detection signal and said delayed detection signal.

5. An image forming method according to claim 4, further comprising a step of:
   injecting a micro bubble contrast medium into said object to be inspected.

6. An image forming method according to claim 1, wherein:
   step (a) includes transmitting to said object to be inspected, an ultrasonic wave which is continued for even-numbered cycles not less than four cycles within a predetermined time duration; and
   step (d) includes obtaining a difference signal between said detection signal and said delayed detection signal, obtaining information related to an echo production position based upon a difference between said difference signal within a first predetermined time duration and said difference signal within a second predetermined time duration, and also, obtaining sub-harmonic component based upon a summation of said difference signal within the first predetermined time duration and said difference signal within the second predetermined time duration.

7. An image forming method according to claim 6, further comprising a step of:
   obtaining the image information by using amplitudes of signals at respective time instants as luminance values, said signals being acquired by logarithmic amplifying and also envelop-detecting both said difference and said summation.

8. An image forming method according to claim 6, further comprising a step of:
   injecting a micro bubble contrast medium into said object to be inspected.

9. An ultrasonic diagnostic apparatus comprising:

first means for transmitting an ultrasonic wave, which is continued for at least two cycles, to an object to be inspected, and for detecting an echo signal which is produced by reflection of the transmitted ultrasonic wave from tissue of said object to be inspected to thereby obtain a detection signal;

second means for delaying said detection signal by such a time duration corresponding to one cycle of the transmitted ultrasonic wave to thereby obtain a delayed detection signal; and third means for obtaining image information related to the tissue of said object to be inspected based upon a difference between said detection signal and said delayed detection signal.

10. An ultrasonic diagnostic apparatus according to claim 9, wherein:

said first means transmits to said object to be inspected, an ultrasonic wave which is continued for at least N/2 cycles within a predetermined time duration where N is an integer not less than four;

said third means obtains a difference signal between said detection signal and said delayed detection signal and obtain, when N is equal to an even number, image information related to the tissue of said object to be inspected based upon a difference between said difference signal within a first predetermined time duration and said difference signal within a second predetermined time duration, whereas obtains, when N is equal to an odd number, image information related to the tissue of said object to be inspected based upon a summation of said difference signal within the first predetermined time duration and the difference signal within the second predetermined time duration.

11. An ultrasonic diagnostic apparatus according to claim 10, wherein:

said third means obtains image information by using amplitudes of a signal at respective time instants as luminance values, said signal being acquired by logarithmic amplifying and also envelope-detecting one of said difference and said summation.

12. An ultrasonic diagnostic apparatus according to claim 9, wherein:

said first means transmits to said object to be inspected, an ultrasonic wave which is continued for at least four cycles; and said third means extracts a sub-harmonic component of said echo signal based upon the difference between said detection signal and said delayed detection signal.

13. An ultrasonic diagnostic apparatus according to claim 9, wherein:

said first means transmits to said object to be inspected, an ultrasonic wave which is continued for even-numbered cycles not less than four cycles within a predetermined time duration; and said third means obtains a difference signal between said detection signal and said delayed detection signal, obtains information related to an echo production position based upon a difference between said difference signal within a first predetermined time duration and said difference signal within a second predetermined time duration, and also, obtains a sub-harmonic component based upon a summation of said difference signal within the first predetermined time duration and said difference signal within the second predetermined time duration.

14. A signal processing apparatus for processing a detection signal which is obtained by that an ultrasonic wave continued for at least two cycles is transmitted to an object to be inspected and an echo signal produced by reflection of the transmitted ultrasonic wave from tissue of said object to be inspected is detected, said apparatus comprising:

first means for delaying said detection signal by such a time duration corresponding to one cycle of the transmitted ultrasonic wave to thereby obtain a delayed detection signal; and second means for obtaining image information related to the tissue of said object to be inspected based upon a difference between said detection signal and said delayed detection signal.

15. A signal processing apparatus according to claim 14, wherein:

said first means processes a detection signal which is obtained by detecting an echo signal produced by reflection of the transmitted ultrasonic wave from the tissue of said object to be inspected, said ultrasonic wave being continued for at least N/2 cycles within a predetermined time duration where N is an integer not less than four; and said second means obtains a difference signal between said detection signal and said delayed detection signal, and obtains, when N is equal to an even number, image information related to the tissue of said object to be inspected based upon a difference between said difference signal within a first predetermined time duration and said difference signal within a second predetermined time duration, whereas obtains, when N is equal to an odd number, image information related to the tissue of said object to be inspected based upon a summation of said difference signal within the first predetermined time duration and said difference signal within the second predetermined time duration.

16. A signal processing apparatus according to claim 14, wherein:

said first means processes a detection signal which is obtained by detecting an echo signal produced by reflection of the transmitted ultrasonic wave from the tissue of said object to be inspected, said ultrasonic wave being continued for at least four cycles; and said second means extracts a sub-harmonic component of said echo signal based upon the difference between said detection signal and said delayed detection signal.

17. A signal processing apparatus according to claim 14, wherein:

said first means processes a detection signal which is obtained by detecting an echo signal produced by reflection of the transmitted ultrasonic wave from the tissue of said object to be inspected, said ultrasonic wave being continued for even-numbered cycles not less than four cycles within a predetermined time duration; and said second means obtains a difference signal between said detection signal and said delayed detection signal, obtains information related to an echo production position based upon a difference between said difference signal within a first predetermined time duration and said difference signal within a second predetermined time duration, and also, obtains a sub-harmonic component based upon a summation of said difference signal within the first predetermined time duration and said difference signal within the second predetermined time duration.

18. A recording medium readable by a CPU (central processing unit) and recording a signal processing program for processing a detection signal which is obtained by that an ultrasonic wave continued for at least N/2 cycles within a predetermined time duration is transmitted to an object to be inspected and an echo signal produced by reflection of the transmitted ultrasonic wave from tissue of said object to be inspected is detected where N is an integer not less than four, said signal processing program causing said CPU to execute:

delaying said detection signal by such a time duration corresponding to one cycle of the transmitted ultrasonic wave to thereby obtain a delayed detection signal;

obtaining a difference signal between said detection signal and said delayed detection signal;

obtaining, when N is equal to an even number, image information related to the tissue of said object to be inspected based upon a difference between said difference signal within a first predetermined time duration and said difference signal within a second predetermined time duration; and obtaining, when N is equal to an odd number, image information related to the tissue of said object to be inspected based upon a summation of said difference signal within the first predetermined time duration and said difference signal within the second predetermined time duration.

19. A recording medium readable by a CPU (central processing unit) and recording a signal processing program for processing a detection signal which is obtained by that an ultrasonic wave continued for at least four cycles is transmitted to an object to be inspected and an echo signal produced by reflection of the transmitted ultrasonic wave from tissue of said object to be inspected is detected, said signal processing program causing said CPU to execute:

delaying said detection signal by such a time duration corresponding to one cycle of the transmitted ultrasonic wave to thereby obtain a delayed detection signal; and extracting a sub-harmonic component of said echo signal based upon a difference between said detection signal and said delayed detection signal.

20. A recording medium readable by a CPU (central processing unit) and recording a signal processing program for processing a detection signal which is obtained by that an ultrasonic wave continued for at least four cycles within a predetermined time duration is transmitted to an object to be inspected and an echo signal produced by reflection of the transmitted ultrasonic wave from tissue of said object to be inspected is detected, said signal processing program causing said CPU to execute:

delaying said detection signal by such a time duration corresponding to one cycle of the transmitted ultrasonic wave to thereby obtain a delayed detection signal;

obtaining a difference signal between said detection signal and said delayed detection signal;

obtaining information related to an echo production position based upon a difference between said difference signal within a first predetermined time duration and said difference signal within a second predetermined time duration; and obtaining a sub-harmonic component based upon a summation of said difference signal within the first predetermined time duration and said difference signal within the second predetermined time duration.

* * * * *